United States Patent [19]
Dauth et al.

[11] Patent Number: 5,705,589
[45] Date of Patent: Jan. 6, 1998

[54] ORGANOSILANE AND ORGANOPOLYSILOXANE FREE RADICAL INITIATORS AND MACROMONOMERS AND GRAFT COPOLYMERS WHICH CAN BE PREPARED WITH THEM

[75] Inventors: Jochen Dauth, Burchausen; Bernward Deubzer, Burghausen; Oskar Nuyken, München; Brigette Voit, München; Ralf Kollefrath, München, all of Germany

[73] Assignee: Wacker-Chemie GmbH, Munich, Germany

[21] Appl. No.: 501,750

[22] Filed: Jul. 12, 1995

[30] Foreign Application Priority Data

Jul. 28, 1994 [DE] Germany .......................... 44 26 832.7

[51] Int. Cl.$^6$ ............................................................ C08G 77/452
[52] U.S. Cl. ....................... 528/28; 528/15; 528/25; 528/26; 528/31; 556/413; 556/475
[58] Field of Search .............................. 528/25, 15, 31, 528/28; 556/413, 475

[56] References Cited

U.S. PATENT DOCUMENTS

| 4,316,041 | 2/1982 | Totten et al. ........................ 556/420 |
| 4,595,740 | 6/1986 | Panster ................................. 528/30 |
| 4,826,954 | 5/1989 | Suzuki et al. ........................ 528/15 |
| 5,098,978 | 3/1992 | Riepl et al. ........................... 528/15 |
| 5,274,053 | 12/1993 | Kurata et al. ....................... 525/479 |

FOREIGN PATENT DOCUMENTS

| 0098947 | 1/1984 | European Pat. Off. . |
| 0539901 | 5/1993 | European Pat. Off. . |
| 2209169 | 5/1989 | United Kingdom . |

Primary Examiner—Ralph H. Dean
Attorney, Agent, or Firm—Martin Connaughton

[57] ABSTRACT

The organosilanes and organopolysiloxanes containing groups which form free radicals and are soluble in organic solvents, processes for their preparation, macromonomers and graft copolymers from the organosilanes and organopolysiloxanes according to the invention as free radical initiators and organic monomers which can be polymerized by free radicals, a process for the preparation of the macromonomers and graft copolymers and their use.

7 Claims, No Drawings

ORGANOSILANE AND ORGANOPOLYSILOXANE FREE RADICAL INITIATORS AND MACROMONOMERS AND GRAFT COPOLYMERS WHICH CAN BE PREPARED WITH THEM

FIELD OF INVENTION

The present invention relates to organosilanes and organopolysiloxanes which contain groups which form free radicals and are soluble in organic solvents, processes for their preparation, macromonomers and graft copolymers from the organosilanes and organopolysiloxanes according to the invention as free radical initiators and organic monomers which can be polymerized by free radicals, a process for the preparation of the macromonomers and graft copolymers and their use.

BACKGROUND OF INVENTION

One possibility for the preparation of graft copolymers comprises grafting with reactive monomers a polymer which carries a functional end group capable of reaction. This is called the "grafting onto" process. For example, in EP-A-539 901, vinyl monomers are grafted by the emulsion polymerization process onto an emulsified organopolysiloxane which contains binding sites. The binding sites are generated by dialkoxysilanes which are co-condensed into the organopolysiloxane and contain a radical which forms free radicals. In this "grafting onto" process, homopolymerization of the organic monomers is started by means of an external redox initiator system, and the growing organopolymer chains bind to the binding sites of the organopolysiloxane graft base.

An obvious disadvantage of this process is that binding of the organopolymer to the organopolysiloxane does not necessarily occur, and a considerable portion of the organic polymer is therefore not grafted onto the polysiloxane, but is present as non-bound homopolymer. A further disadvantage of the "grafting onto" process is that as a result of intramolecular linkages, in particular loops caused by multiple binding of the organopolymer chain to the organosilicon polymer core, graft copolymers which are built up in an uncontrolled manner are formed, as can be demonstrated by structural characterization of such graft copolymers, for example by means of static and dynamic light scattering.

The object was to provide organosilanes and organopolysiloxanes which have groups which form free radicals, can be prepared in a readily reproducible and simple manner and with which it is possible to synthesize, by free radical polymerization, macromonomers and graft copolymers which do not have the above mentioned disadvantages of the known graft copolymers, or a high content of organopolymer homopolymer and an uncontrolled build-up.

SUMMARY OF INVENTION

The present invention relates to organosilanes and organopolysiloxanes containing groups which form free radicals and being built up from 0.1% to 100.0% by weight of units of the formula

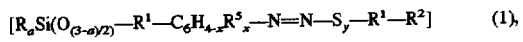

0% to 80.0% by weight of units of the formula $[R^2{}_3SiO_{1/2}]$  (2),

0% to 99.9% by weight of units of the formula $[R^2{}_2SiO_{2/2}]$  (3),

0% to 80.0% by weight of units of the formula $[R^2SiO_{3/2}]$  (4)

and
0% to 80.0% by weight of units of the formula $[SiO_{4/2}]$  (5), in which

R is identical or different chlorine or bromine atoms, hydroxyl groups, $C_1$- to $C_{18}$-alkoxy radicals, or monovalent $C_1$- to $C_{18}$-hydrocarbon radicals which are optionally substituted by halogen atoms, amino groups, hydroxyl groups, epoxyalkyl radicals or cyano groups, $R^1$ is a chemical bond, or identical or different divalent $C_1$- to $C_{18}$-hydrocarbon radicals which are optionally substituted by halogen atoms, amino groups, hydroxyl groups, acyloxy groups, epoxyalkyl radicals or cyano groups and can be interrupted by divalent radicals, bonded to carbon atoms on both sides, from the group consisting of —O—, —S—, —COO—, —OOC—, —CONR$^2$—, —NR$^2$CO—, —NR$^2$— and —CO—, $R^5$ is identical or different halogen atoms, cyano groups, nitro groups, or radicals —R, —OR or —C(O)R, $R^2$ is a hydrogen atom or a radical R and a is 0, 1, 2 or 3, x is 0, 1, 2, 3 or 4 and y is 0 or 1, with the proviso that if 100% by weight of units of formula (1) are present, a has the value 3.

Examples of unsubstituted radicals R are alkyl radicals, such as the methyl, ethyl, n-propyl, iso-propyl, n-butyl, iso-butyl, tert-butyl, n-pentyl, iso-pentyl, neo-pentyl and tert-pentyl radical, hexyl radicals, such as the n-hexyl radical, heptyl radicals, such as the n-heptyl radical, octyl radicals, such as the n-octyl radical and iso-octyl radicals, such as 2,2,4-trimethylpentyl radical, nonyl radicals, such as the n-nonyl radical, decyl radicals, such as the n-decyl radical, dodecyl radicals, such as the n-dodecyl radical and octadecyl radicals; such as n-octadecyl radical; alkenyl radicals, such as the vinyl, allyl, n-5-hexenyl, 4-vinylcyclohexyl and the 3-norbornenyl radical; cycloalkyl radicals, such as cyclopentyl, cyclohexyl, 4-ethylcyclohexyl and cycloheptyl radicals, norbornyl radicals and methylcyclohexyl radicals; aryl radicals, such as the phenyl, biphenylyl, naphthyl, anthryl and phenanthryl radical; alkaryl radicals, such as o-, m- and p-tolyl radicals, xylyl radicals and ethylphenyl radicals; and arallcyl radicals, such as the benzyl radical and the α,β-phenylethyl radical.

Examples of substituted hydrocarbon radicals as the radical R are halogenated hydrocarbons, such as the chloromethyl, 3-chloropropyl, 3-bromopropyl, 3,3,3-trifluoropropyl and 5,5,5,4,4,3,3-heptafluoropentyl radical and the chlorophenyl, dichlorophenyl and trifluorotolyl radical; mercaptoalkyl radicals, such as the 2-mercaptoethyl and 3-mercaptopropyl radical; cyanoalkyl radicals, such as the 2-cyanoethyl and 3-cyanopropyl radical; aminoalkyl radicals, such as the 3-aminopropyl, N-(2-aminoethyl)-3-aminopropyl- and N-(2-aminoethyl)-3-amino-(2-methyl) propyl radical; aminoaryl radicals, such as the aminophenyl radical; acyloxyalkyl radicals, such as the 3-acryloyloxypropyl and 3-methacryloyloxypropyl radical; hydroxyalkyl radicals, such as the hydroxypropyl radical, and radicals of the formulae

 and HOCH₂CH(OH)CH₂SCH₂CH₂—.

The radical R is preferably the methyl, ethyl, n-propyl, vinyl, 3-norbornenyl, n-5-hexenyl, tolyl and phenyl radical, in particular the methyl and vinyl radical. If formula (1) describes organosilanes, the radical R is also preferably chlorine atoms and methoxy and ethoxy groups.

In formula (1) the azo group can be bonded to the aromatic in the ortho-, meta- or para- position. If $R^1$ is a chemical bond the silicon atoms and the group $C_6H_{4-x}$ are directly linked.

Examples of substituents from the divalent hydrocarbon radicals $R^1$ are halogen atoms, cyano groups and $C_1$-$C_6$-acyloxy radicals. Examples of divalent hydrocarbon radicals $R^1$ are saturated, branched or unbranched alkylene radicals, such as the methylene and ethylene radical, as well as propylene, butylene, pentylene, 1-methylpentylene, hexylene, cyclohexylene and octadecylene radicals, or unsaturated alkylene or arylene radicals, such as the hexenylene radical, phenylene radicals, such as the 2-chloro-1, 4-phenylene radical, and in particular radicals of the formulae

 (6)

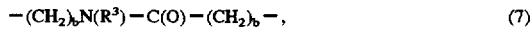 (7)

 (8)

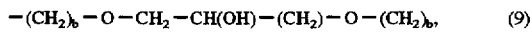 (9)

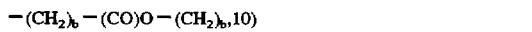 (10)

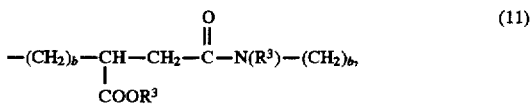 (11)

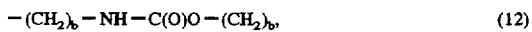 (12)

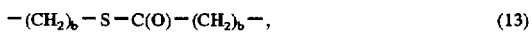 (13)

in which $R^3$ is a hydrogen atom or identical or different monovalent SiC-bonded, optionally substituted $C_1$-$C_6$-hydrocarbon radicals and b is an integer having a value from 0 to 16, preferably 0 to 6.

Preferred examples of terminal groups —$R^1$—$R^2$ are radicals of the formulae —C(CN)₂CH₃, —C(CH₃)₂CN, —C(C₆H₅)₂Cl, —C(C₆H₅)₂OAc, —C(C₆H₅)CH₃Cl, —C(C₆H₅)CH₃OAc, —C₆H₅, and —S—C₆H₅.

x is preferably 0, 1 or 2.

The organopolysiloxanes containing groups which form free radicals preferably comprise 0.5% to 20.0% by weight, in particular 1.0% to 10.0% by weight, of units of formula (1).

The organopolysiloxanes containing groups which form free radicals can contain up to 90.0% by weight of units of formula (3) if the organopolysiloxanes are present as cyclic compounds. The organopolysiloxanes containing groups which form free radicals comprise 20.0% to 99.0% by weight, in particular 50.0% to 99.0% by weight, of units of formula (3).

In a preferred embodiment, the organopolysiloxanes containing groups which form free radicals contain at least 90.0% by weight, in particular 95.0% by weight, of units of formula (3), and the remaining units are units of formulae (2) and (1), in which a has the value 1. These organopolysiloxanes have a linear, comb-like structure. The binding sites on the units of formula (1) are particularly easily accessible for the reaction with organic monomers which can be polymerized by means of free radicals.

The organopolysiloxanes containing groups which form free radicals can also comprise, for example, at least 90.0% by weight of units of formulae (2), (4) and (5). They are then resins. The organopolysiloxanes containing groups which form free radicals preferably comprise not more than 80.0% by weight, in particular 50.0% by weight, and more preferably not more than 20.0% by weight, of units of formulae (4) or (5).

The organopolysiloxanes containing groups which form free radicals are preferably linear organopolysiloxanes or elastomers which contain hydrogen atoms and methyl or vinyl radicals as some of the radicals $R^2$.

Preferably, at least 15 g, in particular 30 g, of the organopolysiloxanes containing groups which form free radicals are soluble in 100 ml of toluene at 20° C. The organopolysiloxanes containing groups which form free radicals are also readily soluble in other organic solvents, such as dioxane and tetrahydrofuran (THF), and are therefore particularly suitable for use as free radical macroinitiators for grafting polymerization in solution.

The average molecular weights of the organopolysiloxanes containing groups which form free radicals are preferably $10^3$ to $10^5$ g/mole, in particular $5 \times 10^3$ to $5 \times 10^4$ g/mole.

The invention also relates to processes for the preparation of the organosilanes and organopolysiloxanes containing groups which form free radicals.

Process I

In this process, organosilanes and organopolysiloxanes built up from 0.1% to 100.0% by weight of units of the formula

 (14), and the amounts of units of formulae (2) to (5) stated above for the organosilanes and organopolysiloxanes containing groups which form free radicals, are reacted with compounds of the formula

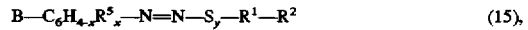 (15), in which

A is identical or different monovalent $C_1$- to $C_{17}$-hydrocarbon radicals which contain a carboxylic acid anhydride or epoxide group or a group —COCl or —NCO and are optionally substituted by halogen atoms, amino groups, hydroxyl groups, epoxy alkyl radicals or cyano groups, and can be interrupted by divalent radicals, bonded to carbon atoms on both sides, from the group consisting of —O—, —S—, —COO—, —OOC—, —CONR²—, —NR²CO—, —NR²— and —CO—, B is the group —(CH₂)$_c$OH, —(CH₂)$_c$NHR¹, —(CH₂)$_c$COOH, —(CH₂)$_c$SH, c is an integer having a value from 0 to 10 and R, $R^5$, a, x, y, $R^1$ and $R^2$ have the above meanings, with the proviso that the sum of the carbon atoms in A and B is not more than 18.

The invention also relates to process (II) a corresponding process for the preparation of the organosilanes and organopolysiloxanes containing groups which form free radicals in formulae (14) and (15)above.

B is a carboxylic acid anhydride or epoxide group, a group —COCl, —COOH or —NCO, or identical or different monovalent $C_1$- to $C_{17}$-hydrocarbon radicals which contain a carboxylic acid anhydride or epoxide group or a group —COCl or —NCO and are optionally substituted by halogen atoms, amino groups, hydroxyl groups, epoxyalkyl radicals or cyano groups and can be interrupted by divalent radicals, bonded to carbon atoms on both sides, from the group consisting of —O—, —S—, —COO—, —OOC—, —CONR$^2$—, —NR$^2$CO—, —NR$^2$— and —CO—, A is the group —(CH$_2$)$_c$OH, —(CH$_2$)$_c$CH$_2$NHR$^1$, —(CH$_2$)$_c$CH$_2$COOH or —(CH$_2$)$_c$CH$_2$SH and R, a, c, R$^1$ and R$^2$ have the above meanings, with the proviso that the sum of the carbon atoms in A and B is not more than 18.

Process I is preferably carried out in the organic solvents mentioned below for process 2.

If a group —COCl is present in A or B in process 1, the reaction is preferably carried out in the presence of bases, such as triethylamine or pyridine, in order to trap the hydrogen chloride.

Process 2:

—In this process, organosilanes or organopolysiloxanes are built up from 0.1% to 100.0% by weight of units of the formula

[R$_a$SiHO$_{(3-a)/2}$]   (16),

and the amounts of units of formulae (2) to (5) stated above for the organosilanes and organopolysiloxanes containing groups which form free radicals, are reacted in the presence of platinum, rhodium or compounds thereof with compounds of the formula R$^4$—C$_6$H$_{4-x}$R$^5_x$—N=N—S$_y$—R$^1$—R$^2$   (17),

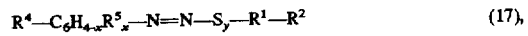

in which

R$^4$ is identical or different monovalent C$_1$- to C$_{18}$-hydrocarbon radicals which contain an olefinic double bond or acetylenic triple bond and are optionally substituted by halogen atoms, amino groups, hydroxyl groups, acyloxy groups, epoxyalkyl radicals or cyano groups and can be interrupted by divalent radicals, bonded to carbon atoms on both sides, from the group consisting of —O—, —S—, —COO—, —OOC—, —CONR$^2$—, —NR$^2$CO—, —NR$^2$— and —CO—, and R, R$^5$, a, x, y, R$^1$ and R$^2$ have the above meanings.

All the catalysts which have been employed to date for addition of hydrogen atoms bonded directly to Si atoms onto aliphatically unsaturated compounds can be employed for the above reaction. Examples of such catalysts are metallic and freely divided platinum, which can be on supports, such as silicon dioxide, aluminum oxide or active charcoal, compounds or complexes of platinum, such as platinum halides, for example PtCl$_4$, H$_2$PtCl$_6$*6H$_2$O and Na$_2$PtCl$_4$*4H$_2$O, platinum-olefin complexes, platinum-alcohol complexes, platinum-alcoholate complexes, platinum-ether complexes, platinum-aldehyde complexes, platinum-ketone complexes, including reaction products of H$_2$PtCl$_6$*6H$_2$O and cyclohexanone, platinum-vinylsiloxane complexes, in particular platinum divinyltetramethyldisiloxane complexes with or without a content of detectable inorganically bonded halogen, bis(gamma-picoline) platinum dichloride, trimethylenedipyridineplatinum dichloride, dicyclopentadieneplatinum dichloride, dimethyl sulfoxideethylene platinum(II) dichloride and reaction products of platinum tetrachloride with olefin and primary amine or secondary amine or primary and secondary amine, such as the reaction product of platinum tetrachloride, dissolved in 1-octene, with sec-butylamine, or ammonium-platinum complexes.

The catalyst is preferably employed in amounts of 0.5 to 500 ppm by weight (parts by weight per million parts by weight), in particular 2 to 400 ppm by weight, calculated as the elemental metal and based on the total weight of the silanes and/or siloxanes present in the reaction mixture and o containing hydrogen atoms bonded directly to silicon atoms.

The reaction mentioned (called hydrosilylation below) can be carried out in the absence or in the presence of solvents, the presence of solvents being preferred.

If solvents are used, solvents or solvent mixtures which are largely inert under the reaction conditions, and in particular those having a boiling point or boiling range of up to 120° C. at 0.1 MPa, are preferred. Examples of such solvents are ethers, such as dioxane, tetrahydrofuran, diethyl ether and diethylene glycol dimethyl ether; chlorinated hydrocarbons, such as methylene chloride, chloroform, carbon tetrachloride, 1,2-di-chloroethane and trichloroethylene; hydrocarbons, such as pentane, n-hexane, hexane isomer mixtures, heptane, octane, wash benzine, petroleum ether, benzene, toluene and xylenes; ketones, such as acetone, methyl ethyl ketone and methyl isobutyl ketone; carbon disulfide and nitrobenzene, dimethylacetamide, dimethylformamide, dimethyl sulfoxide, N-methylpyrrolidone or mixtures of these solvents.

The term solvent does not mean that all the reaction components must dissolve. The reaction can also be carded out in a suspension or emulsion of one or more of the reaction partners. The reaction can also be carried out in a solvent mixture having a miscibility gap, of at least one reaction partner being soluble in each of the phases of the mixture.

The hydrosilylation can be carried out under the pressure of the surrounding atmosphere, of about 0.1 MPa (absolute), but it can also be carried out under higher or lower pressures. Pressures of 0.01 MPa to 1.0 MPa, in particular 0.09 MPa to 0.11 MPa, are preferred.

Process 3

In this process, a mixture of the components (A) organosilanes of the formula

[R$_a$Si(O$_{(3-a)/2}$)—R$^1$—C$_6$H$_{4-x}$R$^5_x$—N=N—S$_y$—R$^1$—R$^2$]   (1),

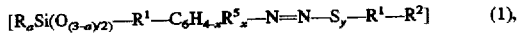

(B) organosilicon compounds which are chosen from (B1) organosilanes of the formula R$^2_d$Si(R$^6$)$_{(4-d)}$   (18)

and (B2) organosiloxanes of units of the formula

R$^2_e$(R$^6$)$_f$SiO$_{(4-e-f)/2}$   (19),

where

R$^6$ is a chlorine or bromine atom or an optionally halogen substituted C$_1$-C$_{10}$-alkoxy radical, d, e and f have the values 0, 1, 2 or 3 and R, R$^1$, R$^2$ and a the above meanings, with the proviso that component B contains at least 0.01 mole of alk oxy groups or chlorine or bromine atoms per mole of silicon atoms, optionally, (C) at least 0.5 mole of water per mole of alkoxy groups, chlorine atoms or bromine atoms in components A and B and optionally (D) a water-miscible solvent, is reacted, The radical R$^5$ is preferably C$_1$-C$_6$-alkyl groups, in particular the methyl, ethyl, n-propyl, iso-propyl and hexyl radical, in particular the methyl and ethyl radical.

Examples of organosiloxanes B1 of formula (18) which can be employed in the process according to the invention are tetramethoxysilane, tetraethoxysilane, tetra-n-propoxysilane, methyltrimethoxysilane, vinyltrimethoxysflane, 3-mercaptopropyl-trimethoxysilane, 3-chloropropyltrimethoxysilane, phenyltrimethoxysilane, o-, m- and p-tolyltrimethoxysilane, propyltrimethoxysilane, methyltriethoxysilane, vinyltriethoxysilane, vinyldimethylethoxysilane, 3-mercaptopropyltriethoxysilane, propyltrimethoxytrimethoxysilane, dimethyldiethoxysilane, dimethyldimethoxysilane and trimethylethoxysilane, where tetraethoxysilane, methyltrimethoxysilane, dimethyldiethoxysilane, vinyldimethylethoxysilane, methyltriethoxysilane, phenyltriethoxysilane, o-, m-, and p-polytriethoxysilane and propyltriethoxysiloxane are preferably employed and tetraethoxysilane is more preferably employed.

The organosiloxanes (B2) which can be employed in the process according to the invention preferably contain not more than 100 units of formula (19). Examples of organosiloxanes (B2) are linear organosiloxanes, such as disiloxanes, for example hexamethyldisiloxane, 1,3-diphenyltetramethyldisiloxane, 1,3-bis(n-5-hexenyl) tetramethyldisiloxane, 1,3-divinyltetramethyldisiloxane, polydimethylsiloxane, polyphenylmethylsiloxane, α,ω-hydroxypolydimethylsiloxane, preferably hexamethyldisiloxane, and 1,3-divinyltetramethyldisiloxane and cyclic organopolysiloxanes of 3 to 8, preferably 4 or 5, units of formula (19), such as hexamethylcyclotrisiloxane, octamethylcyclotetrasiloxane and decamethylcyclopentasiloxane, and polysiloxanes, such as polydimethylsiloxane and α,ω-hydroxypolydimethylsiloxane.

Component (B) can also comprise monomeric and polymeric silicates, for the preparation of resins. Preferred silicates are methyl orthosilicate, ethyl orthosilicate, methyl polysilicate and ethyl polysilicate, the silicates containing alkoxy radicals.

The content of alkoxy groups or chlorine or bromine atoms in component B is preferably 0.5 to 2 mole, in particular 0.65 to 1.5 mole, per mole of silicon atoms.

Preferably at least 0.5 mole, in particular 0.5 to 0.8 mole, of water are employed as component C per mole of alkoxy groups and chlorine or bromine atoms of components A and B.

Organic solvents which mix homogeneously with water in a volume ratio of 1:1 at 20° C. are preferably employed as component D. Examples of solvents suitable as component D are monohydric and polyhydric alcohols, such as methanol, ethanol, n-propanol, iso-propanol and ethylene glycol; ethers, such as dioxane and tetrahydrofuran; amides, such as dimethylformamide; dimethyl sulfoxide and sulfolane or mixtures of these solvents.

Solvents having a boiling point or boiling range of up to 120° C. under 0.1 MPa, in particular the above monohydric alcohols, are more preferred.

Process 3 is preferably carried out in the presence of a catalyst which is known. Examples of catalysts are, sulfuric acid, phosphoric acid, trifluoromethanesulfonic acid, iron (II) chloride, aluminum chloride, boron trifluoride, zinc chloride, kaolin, acid zeolites, sulfonated charcoal, alkali metal hydroxides, preferably potassium hydroxide and cesium hydroxide, alkali metal alcoholates, quaternary ammonium hydroxides, such as tetramethylammonium hydroxide, benzyltrimethylammonium hydroxide and benzyltriethyl-ammonium hydroxide, benzyltrimethylammonium butylate, β-hydroxyethyltrimethyl-ammonium 2-ethylhexoate, quaternary phosphonium hydroxides, such as tetra-n-butylphosphonium hydroxide and tri-n-butyl-3-[tris-(trimethyl-siloxy)silyl]-n-propyl-phosphonium hydroxide, alkali metal siloxanolates and ammonium organosiloxanolates, such as benzyltrimethylammonium-ethyl siloxanolate, and phosphorus-nitrogen compounds, such as phosphonitrile chloride.

The catalyst is preferably employed in amounts of 0.1% to 10% by weight based on the sum of compounds of formulae (1), (18) and (19).

The above preparation processes 1 to 3 are preferably carried out at temperatures of from −10° C. to 80° C., in particular from 0° C. to 60° C. The above preparation processes are preferably carried out with exclusion of light. In the above preparation processes, all the volatile contents and salts are preferably removed after the synthesis.

The organosilanes and organopolysiloxanes containing groups which form free radicals are preferably employed as free radical initiators for the preparation of macromonomers and graft copolymers of ethylenically unsaturated organic monomers.

The invention also relates to a process for the preparation of macromonomers and graft copolymers, in which 95% to 1% by weight of the above organosilanes and organopolysiloxanes containing groups which form free radicals is reacted with 1% to 95% by weight of ethylenically unsaturated monomers.

A macromonomer is a terminal, at least monofunctional reactive polymer. The macromonomers built up here from an organosilane can be condensed or equilibrated to give the graft copolymers.

In the grafting copolymerization process, the graft base to be grafted carries a reactive grouping which reacts with the monomer added for grafting. This process is called the "grafting from" process. When the polymerization starts, the grafted branches grow directly on the graft base, so that graft copolymers and macromonomers having a defined structure can be built up in a specific and controllable manner.

The organosilanes and organopolysiloxanes containing groups which form free radicals can be activated by heating or irradiation. During this process, nitrogen is eliminated and a pair of free radicals formed. The aryl radical bonded to the organopolysiloxane serves as the reactive binding site for the ethylenically unsaturated monomers. The second free radical split off from the organosilane or organopolysiloxane during the activation is so stable that it can polymerize the monomers only to a very small extent. A considerably lower content of free organic-polymer homopolymer is therefore formed than in grafting processes carried out by the "grafting onto" method.

The process for the preparation of macromonomers and graft copolymers can be carried out in bulk or in the presence of organic solvents or in emulsion, it being possible for the organosilanes and organopolysiloxanes containing groups which form free radicals to be partly or completely dissolved. Ethers, such as tetrahydrofuran and dioxane, or hydrocarbons, such as toluene, are preferably employed as solvents. Organic solvents are preferably employed in 0 to 10 times the mount by weight, in particular in 1 to 3 times the amount, of organosilanes and organopolysiloxanes containing groups which form free radicals.

Optionally, the organosilanes and organopolysiloxanes according to the invention can be initially introduced into the reaction vessel together with the solvent. However, all the components of the process can also be mixed, before the free radical macroinitiator is activated.

The reaction is preferably carried out with the exclusion of moisture and oxygen. The reaction mixture is preferably saturated with inert gas, such as nitrogen or argon, for 10 to 90 minutes and the pH should preferably be 7–9 before the free radical initiator is activated.

Grafting onto the free radical initiators is preferably started by increasing the temperature to 40° to 150° C., preferably 40° to 100° C., more preferably 6° to 85° C. Grafting can also be effected by UV irradiation with a mercury or mercury/xenon lamp for up to 24 hours.

Preferably, ethylenically unsaturated organic monomers are metered into the mixture in an amount which is 20% to 80% by weight, based on the total weight of the graft copolymer. Monomers which are preferably employed for the organic polymer content are acrylic acid, methacrylic acid, acrylic acid esters or methacrylic acid esters of aliphatic alcohols and diols having 1 to 10 C atoms, acrylonitrile, styrene, p-methylstyrene, vinyl acetate, vinyl propionate, maleimide, vinylpyrrolidone, vinyl chloride, ethylene, butadiene, isoprene and chloroprene. More preferred monomers are styrene and acrylic acid esters and methacrylic acid ester of aliphatic alcohols having 1 to 4 C atoms, for example methyl (meth)acrylate, ethyl (meth)acrylate or butyl (meth)acrylate, ethylene glycol di(meth)acrylate and ethylene, as well as butadiene. Both homopolymers and copolymers of the monomers mentioned are suitable as the organic polymer content. Grafting polymerization with monomers which contain two ethylenic double bonds leads to crosslinked graft polymers.

For complete polymerization, the start temperature is maintained for 30 minutes to 20 hours, preferably 30 minutes to 8 hours, more preferably 1 to 2 hours. Residual amounts of unreacted organic monomer can then be removed by distillation, optionally together with the solvent, which is preferred. Isolation of the macromonomers and graft copolymers from the solution and removal of residual amounts of unreacted organic monomer are preferably carried out by precipitation in polar solvents, such as ethanol, methanol or water, or by other known purification methods. The macromonomers and graft copolymers are virtually colorless oils or solids.

The invention further relates to the macromonomers and graft copolymers obtainable by the above process.

The molecular weight of graft copolymers according to the invention are preferably $10^4$ to $10^7$ g/mole, in particular $5 \times 10^4$ to $5 \times 10^5$ g/mole.

The macromonomers and graft copolymers prepared by the above process have a defined build-up owing to specific binding of the organopolymer chains to the silicone graft base. The macromonomers and graft copolymers are readily soluble in organic solvents, in particular in the solvents suitable for grafting polymerizations, and can be processed as thermoplastics.

The macromonomers and graft copolymers according to the invention are suitable for use as modified thermoplastics and as compatibility mediators for silicon-containing polymer blends or as the silicone constituent in o polymer blends. Both homopolymers and copolymers of the above mentioned monomers are suitable as the organic polymer content in the thermoplastics and as the organic polymer constituent in the polymer blends.

To prepare the blends, the graft copolymers according to the invention are extruded or subjected to a melt compression moulding operation in amounts of 0.5% to 50% by weight, preferably 3% to 10% by weight, based on the total weight of the blend, with the two corresponding homopolymers. The ratios of the homopolymers with respect to one another can be varied as desired. Combinations of unsaturated ethylene/propy-lene copolymers (EPDM) and silicone polymers are more preferred. By modificiation of rubbers with silicone polymers, the good heat resistance and low-temperature flexibility of the silicones are combined with the good mechanical properties of the rubbers.

In the following examples, in each case unless stated otherwise,
(a) all the amounts are by weight;
(b) all the pressures are 0.10 MPa (absolute);
(c) all the temperatures are 20° C.

The following abbreviations have been used:
of th.=theory
A.G.=analytical grade
conc.=concentrated
GPA=gel permeation chromatography
RI=refractive index
THF=tetrahydrofuran
MMA=methyl methacrylate
PMMA=polymethyl methacrylate
Mn=number average
Mw=weight average EXAMPLES - Organopolysiloxane free radical macroinitiators Example 1

Synthesis of 3-acylchlorophenylazoethane-1,1-dinitrile (Azo I)

60 g of ice are added to 6.31 g ($4.6 \times 10^{-2}$ mole) of 3-aminobenzoic acid, dissolved in a mixture of 100 ml of water and 13 ml of conc. hydrochloric acid and cooled to 0° C. (L1). 3.22 g ($4.6 \times 10^{-2}$ mole) of sodium nitrite in 50 ml of water are cooled to 0° C. (L2). 3.55 g ($4.4 \times 10^{-2}$ mole) of methylmalonodinitrile in 60 ml of ethanol, mixed with a solution of 43.9 g (0.54 mole) of sodium acetate in 100 ml of water, are cooled to 0° C. (L4). L1 is added dropwise to L2, during which the temperature should not rise above 0° C. This suspension (L3) is added dropwise to L4, likewise while cooling with ice. The mixture is stirred at 0° C. for 1 hour and then at room temperature for 30 minutes. The mixture is covered with a layer of diethyl ether in a separating funnel, the aqueous phase is acidified with concentrated HCl and the mixture is shaken. Acid is added until the azo compound has dissolved completely in the ether phase. The organic phase is isolated, washed with water and dried over magnesium sulfate. The solvent is then distilled off and the product, 3-carboxyphenylazoethane-1,1-dinitrile, is dried in vacuo.

Yield: 5.63 g (56% of th.) of 3-carboxyphenylazoethane-1,1-dinitrile. 15.0 g ($6.6 \times 10^{-2}$ mole) of 3-carboxyphenylazoethane-1,1-dinitrile are dissolved in 500 ml of dry toluene and the solution is cooled to 0° C. 13.7 g ($6.6 \times 10^{-2}$ mole) of phosphorus pentachloride, dissolved in 20 ml of methylene chloride, are slowly added dropwise to the mixture so that the reaction temperature does not rise above 40° C. The reaction mixture is then stirred at room temperature for 3 hours. By addition of 2 liter of hexane, the product crystallized out overnight at −20° C., is filtered off with suction under an inert gas and is dried in vacuo.

Yield: 10.3 g (63%) (Azo I)

EXAMPLE 2 - Synthesis of 4-hydroxymethylphenylazoethane-1,1-dinitrile (Azo n)

11.31 g (0.092 mole) of 3-aminobenzylalcohol (L1) are dissolved in 100 ml of water with 13 ml of HCl (con.) and the solution is cooled to 0° C. 6.44 g (0.092 mole) of sodium nitrite are dissolved in 50 ml of water (L2) and the solution is cooled with ice. L2 is slowly added dropwise to L1 so that the reaction temperature does not exceed 0° C. (L3). In the meantime, 7.1 g (0.091 mole) of methylmalonodinitrile and 87.7 g (1.07 mole) of sodium acetate are dissolved in 100 ml of water (L4). L3 is added very rapidly to L4. The reaction solution is stirred at room temperature for 45 minutes and then extracted by shaking 5 times with ether. The combined ether phases are filtered over aluminum oxide and dried over magnesium sulfate and the solvent is distilled off. The product is dissolved in a little methylene chloride (1 part), and 4 to 5 parts of pentane are added. An oily by-product is decanted off. The solution is concentrated and the yellow product which remains is dried in vacuo. Yield: 6 g (30%)

EXAMPLE 3 - Synthesis of amide from Azo I and N-cyclohexylaminopropyldimethoxy-methylsilane (Azo III)

12.3 g (0.05 mole) of N-cyclohexylaminopropyldimethoxy-silane and 13 g (0.11 mole) of trimethylmethoxysilane are initially mixed. A solution of 22 mg ($5.5 \times 10^{-4}$ mole) of sodium hydroxide in 4 ml of water is added dropwise, while stirring continuously. The resulting emulsion is temperature-controlled at 60° C. for 1 hour, whereupon a clear solution is formed. All the highly volatile compounds are distilled off under normal pressure at 100° C. The residue is heated under reflux with 6 ml of 20% strength aqueous hydrochloric acid for 4 hours and the nonaqueous phase is separated off, washed twice with water and distilled under 1 mbar (boiling point 120° to 121° C.). Yield: 5.53 g (31% of th.)

0.68 g ($2.8 \times 10^{-3}$ mole) of Azo I as described in example 1 and 0.28 g ($2.8 \times 10^{-3}$ mole) Of triethylamine are added dropwise to 1 g ($2.8 \times 10^{-3}$ mole) of the bis[tri-methylsiloxy]-N-cyclohexylaminopropylmethylsilanes prepared above, dissolved in 20 ml of THF and cooled to 0° C. The reaction mixture is stirred for one hour. Solid constituents are filtered off and the filtrate is concentrated in vacuo. The residue is taken up in 50 ml of diethyl ether and the mixture is washed twice with 30 ml of water. The organic phase is separated off and dried over sodium sulfate and the solvent is removed to constant weight under a high vacuum at room temperature. Yield: 1.19 g (70% of th.) of a yellow oil are obtained.

EXAMPLE 4 - Synthesis of free radical macroinitiator (RM/1) from Azo I 5.0 g of a polydimethylsiloxane containing N-methylaminopropyl functional groups ($2.6 \times 10^{-3}$ mole of —NHCH$_3$, molecular weight Mn=15,300) are dissolved in 30 ml of dry THF. 0.36 ml ($0.26 \times 2.6 \times 10-3$ mole) of triethylamine and a solution of 0.64 g ($2.6 \times 10^{-3}$ mole) of Azo I in dry THF are added dropwise thereto. The mixture is stirred overnight, the solvent is stripped off down to half at 35° C. in vacuo and the residue is added dropwise to a 2:1 mixture of methanol and water. The resulting emulsion is stirred for one hour and extracted twice by shaking with 100 ml of diethyl ether each time, the combined ether phases are washed with 100 ml of 3% strength NaOH solution and 100 ml of water and dried and the ether is distilled off on a rotary evaporator at 35° C. Viscous, yellow-colored oily product is freed from further ether under a high vacuum. Yield: 4.7 g (85% of th.)

EXAMPLE 5 - Synthesis of free radical macroinitiator (RM/2) from Azo I 20 g of a polydimethylsiloxane containing N=cyclohexylaminopropyl functional groups ($1.3 \times 10^{-2}$ mole of NH-cyclohexyl function, molecular weight Mn=15, 800 g/mole) and the acid chloride Azo I (3.21 g, $1.3 \times 10^{-2}$ mole) of triethylamine are added to the siloxane solution, the mixture is cooled to about 10° C. and the acid chloride solution is added dropwise, while stirring. The mixture is stirred at 10° C. for an additional hour, the solvent is stripped off down to half in vacuo and the residue is added dropwise to 800 ml of methanol. The emulsion is stirred for one hour, the product is sedimented overnight and taken up in THF, and the mixture is dried with MgSO$_4$ and freed from the solvent in vacuo. Yield: 14.3 g (62%)

EXAMPLE 6 - Synthesis of free radical macroinitiator (Rm/3) from Azo I 8 g of a polydimethylsiloxane containing N-cyclohexylaminopropyl functional groups ($2 \times 10^{-3}$ mole of NH-cyclohexyl function, molecular weight Mn - 15,500 g/mole) and 0.5 g of acid chloride Azo I ($2 \times 10^{-3}$ mole) are dissolved in 50 ml each of dry THF. 0.21 g ($2 \times 10^{-3}$ mole) of triethylamine is added to the siloxane solution, the mixture is cooled to about 10° C. and the acid chloride solution is slowly added dropwise, while stirring. The mixture is stirred at 10° C. for an additional hour, the solvent is stripped off down to half in vacuo and the residue is added dropwise to 800 ml of methanol. The emulsion is stirred for one hour, the product is sedimented overnight and taken up in THF and the mixture is dried with MgSO$_4$ and freed from the solvent in vacuo.

Yield: 5.3 g (62%); molecular weight (GPC, THF as the eluent, polystyrene calibration, RI detector): Mn=28,300 Mw=33,700 g/ml

EXAMPLE 7 - Synthesis of free radical macroinitiator (RM/3) from Azo II 5.25 g of untreated aluminum oxide powder (particle size 150 mesh, 58 A) are stirred with 20 ml of ether (absolute) and 0.21 g (1 mmol) of Azo II for 10 minutes. After addition of 3.88 g of a polydimethylsiloxane containing glycidyloxy functional groups (1 mmol of epoxy function, molecular weight - 12600 g/mole), the mixture is stirred for an additional 16 hours. The reaction solution is filtered and the solvent is distilled off in vacuo. The product is obtained as a pale yellow oil. Yield: 1.1 g (27%)

EXAMPLE 8 - Synthesis of 3-vinylphenylazoethane-1,1-dinitrile (AZO IV) 1.19 g (0.01 mole) of 3-aminostyrene are dissolved in 30 ml of water and 5 ml of conc. hydrochloric acid, and 30 g of ice are added. Diazotization is carried out with an ice-cooled solution of 0.7 g (0.01 mole) of NaNO$_2$ in 20 ml of water at 0° C., and the filtered diazonium salt solution is then added dropwise to a solution of 0.8 g (0.01 mole) of methylmalonodinitrile and 10 g (0.12 mole) of sodium acetate in 15 ml of ethanol and 25 ml of water at 0° to 5° C. After the mixture has been stirred at room temperature for 30 minutes, the azo compound is extracted with ether. After purification by column chromatography (70 g of SiO$_2$+10% of H$_2$O, petroleum ether (100 ml)/ether (3 ml)), the substance is obtained as a yellow solid. Yield: 1.8 g (85% of th.)

EXAMPLE 9 - Synthesis of free radical macroinitiator RM/5

2.0 g (9.5 mmole) of 3-vinylphenylazoethane-1,1-dinitrile and 2.88 g of a polyhydridomethylsiloxane having a hydrogen content of 1.6% by weight (corresponds to $4.75 \times 10^{-2}$ mole of HSi units) and a viscosity of 83 mPas at 25° C. are mixed, and 1.44 mg of a divinyltetramethyldisiloxane-platinum complex with 17% by weight of platinum are then added so that the total mixture contains 50 ppm of platinum (based on the pure metal). 5 ml of toluene are also added. The reaction solution is stirred at 45° C. for 16 hours. After a reaction time of two hours, 1.44 mg of the above mentioned catalyst are added. After the end of the reaction, the solution is slowly added dropwise to methanol, a yellow product precipitating. The solid is filtered off and dried to constant weight under a high vacuum. Yield: 4.7 g (96% of th.) of a yellow powder are obtained.

EXAMPLE 10 - Synthesis of free radical macroinitiator RM/6

2.47 g of an α-ω-hydroxypolydimethylsiloxane having a viscosity of 100 mPas at 25° C. and 10 mg ($3.9 \times 10^{-5}$ mole) of tetrabutylammonium hydroxide are added to 0.5 g ($9.5 \times 10^{-4}$ mole) of Azo III as described in Example 3. The reaction mixture is stirred at 45° C. for 24 hours. After cooling to room temperature, the product is taken up in 50 ml of diethyl ethyl and the mixture is extracted twice by shaking with 30 ml of water each time. The organic phase is separated off, dried with sodium sulfate and concentrated to constant weight under a high vacuum at 30° C. Yield: 2.4 g (80% of th.) of a transparent yellow oil are obtained.

EXAMPLE 11a - Grafting copolymerization of RM/1 with MMA in a ratio of 1:3.9 by thermolysis (PC1)

1 g of RM/1 ($4.6 \times 10^{-4}$ mole of azo functions) and 3.9 g ($1.8 \times 10^{-3}$ mole) of MMA are dissolved in 50 ml of toluene. The reaction mixture is degassed thoroughly and then heated at 70° C. for 16 hours. After cooling, the solution is precipitated in 800 ml of methanol. The graft copolymer which has precipitated out is filtered off and dried in vacuo. Yield: 3.5 g (61%)

Molecular weight (GPC, THF as eluent, polystyrene calibration, RI detector): Mn=65,300, Mw=179,100 g/mole.

EXAMPLE 11b - Grafting copolymerization of RM/2 with MMA in a ratio of 1:1 (PC1b)

7.5 g of RM/2 ($4.9 \times 10^{-3}$ mole of azo functions) and 7.5 g of MMA ($7.5 \times 10^{-2}$ mole) are dissolved in 70 ml of toluene. The reaction mixture is degassed thoroughly and then heated at 75° C. for 16 hours. After cooling, the solution is precipitated in 800 ml of methanol. The product which has precipitated out is filtered off and dried in vacuo. Yield: 5.3 g (35%)

Molecular weight (GPC, THF as eluent, polystyrene calibration, RI detector): Mn=19,100, Mw×30,300 g/mole.

EXAMPLE 11c - Grafting copolymerization of RM/2 with MMA in a ratio of 1:10 (PC1c) 1.36 g of RM/2 ($8.9 \times 10^{-4}$ mole of azo functions) and 13.64 g of MMA ($1.36 \times 10^{-2}$ mole) are dissolved in 70 ml of toluene. The reaction mixture is degassed thoroughly and then heated at 75° C. for 16 hours. After cooling, the solution is precipitated in 800 ml of methanol. The product which has precipitated out is filtered off and dried in vacuo. Yield: 11.5 g (76%)

Molecular weight (GPC, THF as eluent, polystyrene calibration, RI detector): Mn=61,700, Mw=114,700 g/mole.

EXAMPLES 11d - Grafting copolymerization of RM/4 with MMA in a ratio of 1:5 (PC1d)

1 g of RM/4 ($2.4 \times 10^{-4}$ mole of azo functions) and 5 g of MMA ($5 \times 10^{-2}$ mole) are dissolved in 70 ml of toluene. The reaction mixture is degassed thoroughly and then heated at 75° C. for 16 hours. After cooling, the solution is precipitated in 800 ml of methanol. The product which has precipitated out is filtered off and dried in vacuo. Yield: 4.81 g (80%)

Molecular weight (GPC, THF as eluent, polystyrene calibration, RI detector): Mn=77,200, Mw=137,100 g/mole.

EXAMPLE 12 - Grafting copolymerization of RM/2 with styrene in a ratio of 1:5 (PC2)

1 g of RM/2 ($6.5 \times 10^{-4}$ mole of azo functions) and 5 g of styrene ($4.8 \times 10^{-2}$ mole) are dissolved in 70 ml of toluene. The reaction mixture is degassed thoroughly and then heated at 90° C. for 16 hours. After cooling, the solution is precipitated in 800 ml of methanol. The product which has precipitated out is filtered off and dried in vacuo. Yield: 3.9 g (65%)

Molecular weight (GPC, THF as eluent, polystyrene calibration, RI detector): Mn=7,600, Mw=19,300 g/mole.

EXAMPLE 13 - Grafting copolymerization of RM/2 with MMA in a ratio of 1:5 by photolysis (PC3)

0.19 g of RM/2 ($1.2 \times 10^{-4}$ mole of azo functions) and 0.94 g of MMA ($9.4 \times 10^{-3}$ mole) are dissolved in 3 ml of toluene. The reaction mixture is degassed thoroughly and then exposed to light with an Hg—Xe high pressure lamp (lamp output=200 W, output to the sample: 100 W/cm$^2$) in a quartz cell under inert gas at 25° C. for 6 hours. After the exposure, the solution is precipitated in 20 ml of methanol. The product which has precipitated out is filtered off and dried in vacuo. Yield: 0.4 g (35%)

Molecular weight (GPC, THF as eluent, polystyrene calibration, RI detector): Mn=16,100, Mw=23,800 g/mole.

EXAMPLE 14 - PMMA/silicone off blend with addition of PC1c 1 g of polydimethylsiloxane (Mn=312,000, Mw=540,000), 9 g of PMMA (Mn=30,200, Mw=50,000) and 0.3 g of PC1c are dissolved in 30 ml of toluene. Films are cast from the solution and these are dried at room temperature for 10 days and then at 40° C. for 2 days. These films show improved mechanical properties in comparison with films of 10% of polydimethylsiloxane and 90% of PMMA without addition of PC1c.

What is claimed is:

1. An organosilane or organopolysiloxane containing groups which form free radicals and consisting essentially of from 0.1% to 100.0% by weight of units of the formula

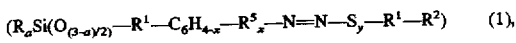

$(R_aSi(O_{(3-a)/2})-R^1-C_6H_{4-x}-R^5_x-N=N-S_y-R^1-R^2)$ (1),

0% to 80.0% by weight of units of the formula

$(R^2_3SiO_{1/2})$ (2),

0% to 99.9% by weight of units of the formula

$(R^2_2SiO_{2/2})$ (3)

0% to 80.0% by weight of units of the formula

$(R^2SiO_{3/2})$ (4)

and

0% to 80.0% by weight of units of the formula $$(SiO_{4/2}) \quad (5),$$

in which

R is identical or different chlorine or bromine atoms, hydroxyl groups, $C_1$- to $C_{18}$-alkoxy radicals, or monovalent $C_1$- to $C_{18}$-hydrocarbon radicals which are optionally substituted by halogen atoms, amino groups, hydroxyl groups, epoxyalkyl radicals or cyano groups, $R^1$ is a chemical bond, or identical or different divalent $C_1$- to $C_{18}$- saturated, optionally branched alkylene radical or an unsaturated alkylene radical which is optionally substituted by halogen atoms, amino groups, hydroxyl groups, acyloxy groups, epoxyalkyl radicals or cyano groups and can be interrupted by divalent radicals, bonded to carbon atoms on both sides, from the group consisting of —O—, —S—, —COO—, —OOC—, —CONR²—, —NR²CO—, —NR²— and —CO—, $R^5$ is identical or different halogen atoms, cyano groups, nitro groups, or radicals —R, —OR or —C(O)R, $R^2$ is a hydrogen atom or a radical R and a is 0, 1, 2 or 3, x is 0, 1, 2, 3 or 4 and y is 0 or 1, with the proviso that if 100% by weight of units of formula (I) are present, a has the value 3.

2. A process for the preparation of an organosilane or organopolysiloxane containing groups which form free radicals as claimed in claim 1, in which an organosilane or organopolysiloxane built up from 0.1% to 100.0% by weight of units of the formula $$(R_aSi(O_{(3-a)/2})-A) \quad (14),$$

and the amounts of units of formulae (2) to (5) are reacted with a compound of the formula $$B-C_6H_{4-x}R^5{}_x-N=N-S_y-R^1-R^2 \quad (15),$$

in which

A is identical or different monovalent $C_1$- to $C_{17}$-hydrocarbon radicals which contain a carboxylic acid anhydride or epoxide group or a group —COCl or —NCO and are optionally substituted by halogen atoms, amino groups, hydroxyl groups, epoxy alkyl radicals or cyano groups, and can be interrupted by divalent radicals, bonded to carbon atoms on both sides, from the group consisting of —O—, —S—, —COO—, —OOC—, —CONR²13 , —NR²CO—, —NR²— and —CO—, B is —(CH₂)$_c$OH, —(CH₂)$_c$NHR¹, —(CH₂)$_c$COOH, —(CH₂)$_c$SH, c is an integer having a value from 0 to 10 and R, $R^5$, a, x, y, $R^1$ and $R^2$ have the above meanings, with the proviso that the sum of the carbon atoms in A and B is not more than 18.

3. A process as claimed in claim 2 for the preparation of an organosilane or organopolysiloxane containing groups which form free radicals as claimed in claim 1, in which, in formulae (14) and (15)

B is a carboxylic acid anhydride or epoxide group, a group —COCl, —COOH or —NCO, or identical or different monovalent $C_1$- to $C_{17}$-hydrocarbon radicals which contain a carboxylic acid anhydride or epoxide group or a group —COCl or —NCO and are optionally substituted by halogen atoms, amino groups, hydroxyl groups, epoxyalkyl radicals or cyano groups and can be interrupted by divalent radicals, bonded to carbon atoms on both sides, from the group consisting of —O—, —S—, —COO—, —OOC—, —CONR²—, —NR²CO—, —NR²— and —CO—, A is —(CH₂)₂OH, —(CH₂)$_c$CH₂NHR¹, —(CH₂)$_c$CH₂COOH or —(CH₂)$_c$CH₂SH and R, a, c, $R^1$ and $R^2$ have the above meanings, with the proviso that the sum of the carbon atoms in A and B is not more than 18.

4. A process for the preparation of an organosilane or organopolysiloxane containing groups which form free radicals as claimed in claim 1, in which an organosilane or organopolysiloxane built up from 0.1% to 100.0% by weight of units of the formula $$(R_aSiH(O_{(3-a)/2}) \quad (16),$$

and the amounts of units of formulae (2) to (5), are reacted in the presence of platinum, rhodium or compounds thereof with compounds of the formula $$R^4-C_6H_{4-x}R^5{}_x-N=N-S_y-R^1-R^2 \quad (17),$$

in which $R^4$ is identical or different monovalent $C_1$- to $C_{18}$-hydrocarbon radicals which contain an olefinic double bond or acetylenic triple bond and are optionally substituted by halogen atoms, amino groups, hydroxyl groups, acyloxy groups, epoxyalkyl radicals or cyano groups and can be interrupted by diva lent radicals, bonded to carbon atoms on both sides, from the group consisting of —O—, —S—, —COO—, —OOC—, —CONR²—, —NR²CO—, —NR²— and —CO—, and R, $R^5$, a, x, y, $R^1$ and $R^2$ have the above meanings.

5. The process for the preparation of an organosilane or organopolysiloxane containing groups which form free radicals as claimed in claim 1, in which a mixture of the components (A) organosilane of the formula $$(R_aSi(O_{(3-a)/2})-R^1-C_6H_{4-x}R^5{}_x-N=N-S_y-R^1-R^2) \quad (1),$$

(B) organosilicon compounds which are chosen from (B1) organosilanes of the formula $$R^2{}_dSi(R^6)_{(4-d)} \quad (18)$$

and (B2) organosiloxanes of units of the formula $$R^2{}_e(R^6)_fSiO_{(4-e-f)/2} \quad (19),$$

where $R^6$ is a chlorine or bromine atom or an optionally halogen-substituted $C_1$–$C_{10}$-alkoxy radical, d, e and f have the values 0, 1, 2 or 3 and R, $R^1$, $R^2$ and a the above meanings, with the proviso that component B contains at least 0.01 mole of alk oxy groups or chlorine or bromine atoms per mole of silicon atoms, optionally, (C) at least 0.5 mole of water per mole of alkoxy groups, chlorine atoms or bromine atoms in components A and B and option ally (D) a water-miscible solvent, is reacted.

6. An organopolysiloxane containing groups which form free radicals as claimed in claim 1, wherein units of formula (1) are present in amounts of from 0.5% to 20% by weight.

7. An organopolysiloxane containing groups which form free radicals as claimed in claim 1, wherein units of formula (3) are present in amounts of at least 90% by weight and remaining units are units of formulae (1) and (2).

* * * * *